(12) United States Patent
Muck (10) Patent No.: US 12,365,589 B2
(45) Date of Patent: *Jul. 22, 2025

(54) PROCESS FOR TREATING WATERS, SOILS, SEDIMENTS AND/OR SLUDGES

(71) Applicant: OASE GmbH, Hörstel-Riesenbeck (DE)

(72) Inventor: Thorsten Muck, Ibbenbüren (DE)

(73) Assignee: OASE GmbH, Hörstel-Riesenbeck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/864,154

(22) Filed: Jul. 13, 2022

(65) Prior Publication Data

US 2023/0033717 A1 Feb. 2, 2023

(30) Foreign Application Priority Data

Jul. 13, 2021 (EP) ...................................... 21185368

(51) Int. Cl.
C12P 3/00 (2006.01)
C01B 25/37 (2006.01)
C02F 1/48 (2023.01)
C02F 1/52 (2023.01)
C02F 1/72 (2023.01)
C02F 11/00 (2006.01)

(52) U.S. Cl.
CPC .............. C01B 25/375 (2013.01); C12P 3/00 (2013.01)

(58) Field of Classification Search
CPC .......... C01B 25/375; C12P 3/00; C02F 1/722; C02F 3/341; C02F 2101/105; C02F 2103/007; C02F 2103/023; C02F 2209/06; C02F 1/488; C02F 1/5236; C02F 2001/5218; C02F 11/004; B09C 1/00; B09C 1/08

See application file for complete search history.

(56) References Cited

U.S. PATENT DOCUMENTS

| | | | |
|---|---|---|---|
| 6,569,342 B1* | 5/2003 | Willuweit et al. ............ | 210/714 |
| 9,174,846 B2 | 11/2015 | Beck et al. | |
| 11,834,355 B2 | 12/2023 | Wilfert et al. | |
| 2003/0189187 A1 | 10/2003 | Hollabaugh et al. | |
| 2023/0050281 A1 | 2/2023 | Muck | |

FOREIGN PATENT DOCUMENTS

| | | |
|---|---|---|
| CN | 1301237 A | 6/2001 |
| CN | 102695760 A | 9/2012 |
| CN | 109456894 A | 3/2019 |
| CN | 110691758 A | 1/2020 |
| CN | 112279478 A | 1/2021 |
| CN | 115244012 A | 10/2022 |
| CN | 115611380 A | 1/2023 |
| DE | 19851345 | 5/2000 |
| EP | 4122895 A1 | 1/2023 |
| WO | WO 95/18070 | 7/1995 |
| WO | WO 99/58457 | 11/1999 |
| WO | WO 01/50863 A1 | 7/2001 |
| WO | WO 2018/169395 A1 | 9/2018 |
| WO | WO 2021/144121 A1 | 7/2021 |

OTHER PUBLICATIONS

Sulu-Gambari F. et al., "Phosphorus Cycling and Burial in Sediments of a Seasonally Hypoxic Marine Basin", Estuaries and Coasts (2018), vol. 41, pp. 921-939. (Year: 2018).*
European Search Report corresponding to European Patent Application No. 22184456.6-1101 dated Jan. 3, 2023 [Machine Translation].
Heinrich et al., "Transformation of redox-sensitive to redox-stable iron-bound phosphorus in anoxic lake sediments under laboratory conditions," Water Res., vol. 189, Article No. 116609 (2021).
Hermans et al., "Coupled dynamics of iron, manganese, and phosphorus in brackish coastal sediments populated by cable bacteria," Liminol. Oceanogr., vol. 66, pp. 2611-2631 (2021).
Hermans et al., "Biogeochemical impact of cable bacteria on coastal Black Sea sediment," Biogeosciences, 17, pp. 5919-5938 (2020).
International Preliminary Report on Patentability Corresponding to International Patent Application No. PCT/EP2020/087301 dated Jul. 19, 2022 (English translation).
International Search Report Corresponding to International Patent Application No. PCT/EP2020/087301 dated Mar. 19, 2021.
Kjeldsen et al., "On the evolution and physiology of cable bacteria." PNAS, vol. 116(38), pp. 19116-19125 (2019).
Muller et al., "Groundwater cable bacteria conserve energy by sulfur disproportionation." ISME J., vol. 14, pp. 623-634 (2019).
Prot et al., "Magnetic separation and characterization of vivianite from digested sewage sludge." Sep. Pur. Tech., vol. 224, pp. 564-579 (2019).
Sulu-Gambari et al., "Cable Bacteria Control Iron-Phosphorous Dynamics in Sediments of a Coastal Hypoxic Basin." Env. Sci. Tech., vol. 50, pp. 1227-1233 (2016).
Wang et al., "Fe(III) reduction and vivianite formation in activated sludge," Separation and Purification Technology, 220, pp. 126-135 (2019).
Written Opinion of the International Searching Authority Corresponding to International Patent Application No. PCT/EP2020/087301 dated Mar. 19, 2021 (English translation).

(Continued)

*Primary Examiner* — Satyendra K Singh
(74) *Attorney, Agent, or Firm* — Jenkins, Taylor & Hunt, P.A.

(57) ABSTRACT

The present invention relates to a process for forming or obtaining vivianite in or from a phosphorus-containing waterbody, sediment and/or sludge, to an apparatus for obtaining vivianite from a phosphorus-containing waterbody, sediment and/or sludge, and to the use of a composition comprising at least one alkaline earth metal peroxide and a magnetic separating apparatus for obtaining vivianite from a phosphorus-containing waterbody, sediment and/or sludge.

15 Claims, 1 Drawing Sheet

(56) References Cited

OTHER PUBLICATIONS

Yuan et al., "Biosynthesis of vivianite from microbial extracellular electron transfer and environmental application," Science of the Total Environment, 762, 143076, pp. 1-13 (2021).
Office Action and Search report received in Chinese Patent Application No. 202210826847.X mailed on May 9, 2024, 18 pages. (Translation).
Office Action received in Chinese Patent Application No. 202080098421.6. mailed on Dec. 22, 2023, 13 pages. (Translation).
Scholz, V.V., et al., "The rhizosphere of aquatic plants is a habitat for cable bacteria", FEMS Microbiology Ecology, vol. 95, No. 6, May 4, 2019, 9 pages.
Intention to grant of a European patent corresponding to European Patent Application No. 22184456.6-1014 dated Dec. 20, 2024, pp. 16 (Translation).
Office Action and Search Report received in Chinese Patent Application No. 202080098421.6, mailed on Aug. 12, 2024 (machine translation).
Office Action (Restriction Requirement) corresponding to U.S. Appl. No. 17/792,660 dated Jan. 29, 2025.

\* cited by examiner

PROCESS FOR TREATING WATERS, SOILS, SEDIMENTS AND/OR SLUDGES

CROSS-REFERENCE TO RELATED APPLICATIONS

This application claims priority to European Patent Application No. 21185368.4, filed Jul. 13, 2021, the disclosure of which is incorporated herein by reference in its entirety.

TECHNICAL FIELD

The present invention relates to a process for forming and obtaining vivianite in or from a phosphorus-containing waterbody, sediment and/or sludge, to an apparatus for obtaining vivianite from a phosphorus-containing waterbody, sediment and/or sludge, and to the use of a composition comprising at least one alkaline earth metal peroxide and of a magnetic separating apparatus for obtaining vivianite from a phosphorus-containing waterbody, sediment and/or sludge.

BACKGROUND

A consequence of high phosphorus loading (eutrophication) in seas, lakes and waterbodies is the accelerated formation of sludge from Particulate Organic Material (POM) such as dead algae and plant parts which have not fully mineralized.

In this case there may be a natural formation in the sludge, owing to the presence of Fe ions, of vivianite ($Fe(II)_3(PO_4)_2 \cdot 8H_2O$), which in this case is able to bind the phosphorus, as described for instance in L. Heinrich et al., Water Research 189 (2021), 116609. In this way it is possible to achieve phosphorus binding in waters, and to counteract eutrophication. Specific formation of vivianite, however, has not been achieved.

Furthermore, vivianite has also been found in wastewaters, from which it can also be removed, as described in T. Prot et al., Separation and Purification Technology, DOI: https://doi.org/10.1016/j.seppur.2019.05.057. For waterbodies, sediments and sludges in a natural environment, however, this is difficult to accomplish, owing to the complex events in the ecosystem.

Because of its importance as a basic material for the production of secondary lithium batteries, for example for the preparation of lithium iron phosphate, however, vivianite is also of economic interest, as well as being used as a colorant.

SUMMARY

It is an object of the present invention, therefore, to provide for phosphorus removal from waterbodies, sludges and/or sediments that yields reproducibly good results and generates a substance of value.

It has surprisingly been found that by adding a composition comprising at least one alkaline earth metal peroxide into and/or to a waterbody, a sediment and/or a sludge, it is possible to force the formation of vivianite, after which vivianite can easily be removed magnetically.

A first aspect of the present invention relates to a process for obtaining vivianite from a phosphorus-containing waterbody, sediment and/or sludge, comprising:

(a) introducing and/or applying a composition comprising at least one alkaline earth metal peroxide into and/or to the waterbody, the sediment and/or the sludge;

(b) forming vivianite in the waterbody, sediment and/or sludge; and (c) optionally magnetically removing the vivianite from the waterbody, sediment and/or sludge.

Disclosed in a second aspect is an apparatus for obtaining vivianite from a phosphorus-containing waterbody, sediment and/or sludge, comprising:

(i) a device for introducing and/or applying a composition comprising at least one alkaline earth metal peroxide, configured to introduce the composition comprising at least one alkaline earth metal peroxide into the waterbody, the sediment and/or the sludge and/or to apply it to the waterbody, the sediment and/or the sludge; and (ii) a magnetic separating apparatus comprising a magnet, configured to remove the vivianite from the waterbody, sediment and/or sludge.

In addition the invention relates to the use of a composition comprising at least one alkaline earth metal peroxide and of a magnetic separating apparatus for obtaining vivianite from a phosphorus-containing waterbody, sediment and/or sludge.

Advantageous embodiments and developments are apparent from the further, dependent claims and also from the description with reference to the figures.

BRIEF DESCRIPTION OF THE DRAWINGS

The appended figures are intended to convey a further understanding of the embodiments of the invention. They illustrate embodiments and serve, in association with the description, to explain principles and concepts of the invention. Other embodiments and many of the stated advantages are apparent in relation to the drawings. The elements in the drawings are not necessarily shown in true scale relative to one another.

In the figures of the drawing, elements, features and components which are identical, functionally identical and of identical effect are each provided—unless observed otherwise—with the same reference symbols.

DETAILED DESCRIPTION

Definitions

First of all, in the context of the present patent application, the following terms are to be understood as follows:

Unless otherwise defined, technical and scientific expressions used herein have the same meaning as that commonly understood by a person skilled in the art in the field of the invention.

Cable bacteria are multicellular bacteria which are arrayed like chains and so form long cable-like assemblies which bring about electron transport over centimetre distances. They belong to the Desulfobulbaceae family of deltaproteobacteria, which are known to comprise sulfate-reducing or sulfur-disproportionating species. According to their 16S rRNA, cable bacteria are presently considered to form two genera, "Candidatus electrothrix" and "Candidatus electronema". With an "anodic end" deep in the sediment and a "cathodic end" at the phase boundary with electron acceptors, they are able to bridge suboxic zones and in the anoxic zone to carry out oxidation, for example, of sulfide to sulfate. At the "cathodic end" (functioning as cathode) is a reduction, for example, of oxygen, leading there to a rise in pH. The cable bacteria enable electronic transport over long distances. It is significant that these cable bacteria typically lack sufficient stability to grow out of the sediment surface, in order to reach the oxygen dissolved in the water. Cable bacteria accordingly are unable to operate in the strongly reducing sediments of eutrophic waterbodies. Through their electron transport, they provide spatial bridging between the incidence of substrate and electron acceptor. This makes them significantly superior to other organisms, which are only able to metabolise directly at the boundary layer of the redox potentials.

In the waterbodies which have sludged up as a result of eutrophication, therefore, cable bacteria are of course unable to "work" since in such waterbodies the oxygen, as electron acceptor, does not reach the upper sediment layer. With the aid of calcium peroxide, these generally natural organisms are able to switch off the known competition principle which is based on the respectively highest redox potentials of the respective electron acceptors; cable bacteria short-circuit directly with the respectively highest redox potential present and so circumvent microbiological competition with microorganisms which are confined to metabolism at/in the phase boundary.

The oxidation of sulfide eliminates its phytotoxic effect and hence enables underwater plants to colonise and grow. The loss of macrophyte vegetation in waterbodies, indeed, is a known and unwelcome consequence of eutrophication.

In this way cable bacteria decouple Fe(II) from a sulfidic fixture. Mobilized Fe(II) accumulates in the pore water and hence also arrives at the phase boundary between sediment and body of water, where it is normally oxidized by oxygen to Fe(III), which, as is known, can bind or adsorb phosphate. Bonds of this kind between phosphate and iron are unstable with respect to anoxic conditions and then are broken again with release of P (iron-phosphorus cycle).

A further advantage of the cable bacteria is that they are mobile and are able to adopt an orientation, in sludges and/or sediments, for example, and even on particles, in order thus to be able to perform a redox reaction in a variety of environments.

Cable bacteria are described for example in K. U. Kjeldsen et al., "On the evolution and physiology of cable bacteria", PNAS, 2019, www.pnas.org/cgi/doif1073/pnas.1903514116, with this article being referenced in relation to the cable bacteria and the content thereof in respect of cable bacteria being hereby incorporated by reference.

Surprisingly the natural process of Fe oxidation and unstable P binding can be diverted by a prior treatment of the sediment with alkaline earth metal peroxide, more particularly calcium peroxide, in such a way that formation of vivianite occurs instead. It is known that calcium peroxide with phosphate leads to the formation of apatite. Under the conditions of a decoupling of the iron-sulfide fixture by cable bacteria, in particular, a flow of Fe(II) to the primary reaction product apatite leads to recrystallization with vivianite as the end product, with displacement of the alkaline earth metal, more particularly calcium.

In the sulfide-free, anoxic pore water, the Fe(II) and further phosphate from the reduction of Fe(III) phosphates are additionally able to crystallize on these "seed crystals". Since vivianite is insoluble and stable under all environmental conditions, the natural process (with unstable phosphorus fractions) is diverted accordingly into the formation of a lastingly stable sink for iron and phosphorus.

Waterbodies or waters in the sense of the present invention are all waters or waterbodies, such as ponds, lakes, rivers, reservoirs, nearshore waterbodies, fjords, brackish-water lakes, bays, lake water, breeding stations for fish and other marine animals, water in storage systems for agriculture or drinking-water reservoirs, and aquifers, and the waters present may also contain soils, sediments and/or sludges and also sunken and suspended matter. Sediments in the sense of the present invention are understood to be solid elements present in waters, such as in ponds, lakes and rivers, for example. The sludges may originate, for example, from sewage treatment plants, wastewater filters, etc. and/or may be located on the bottom of waters. Preferred waters are fresh waters with sediments and/or sludge deposits, such as, for instance, ponds, lakes, etc., which may have suboxic and/or anoxic zones and may undergo rapid tipping, but which can be treated effectively with the present processes. According to certain embodiments, the waterbodies or waters have anoxic zones so and/or anoxic zones are generated, for example by removal of dissolved oxygen and/or by addition of reducing agents such as dithionite, for example sodium dithionite, and more particularly the anoxic zones contain Fe ions, more particularly Fe(II), although this is customarily the case in waterbodies or waters.

Amounts in the context of the present invention refers to wt %, unless otherwise indicated or evident from the context.

In a first aspect the present invention relates to a process for forming or obtaining vivianite in or from a phosphorus-containing waterbody, sediment and/or sludge, comprising:
(a) introducing and/or applying a composition comprising at least one alkaline earth metal peroxide into and/or to the waterbody, the sediment and/or the sludge;
(b) forming vivianite in the waterbody, sediment and/or sludge; and
(c) optionally magnetically removing the vivianite from the waterbody, sediment and/or sludge.

According to certain embodiments, in the process of the invention, step (c), the magnetic removal of the vivianite from the waterbody, sediment and/or sludge, is carried out; i.e. step (c) is essential.

The influence of cable bacteria on the fixation of phosphorus in waterbodies is the basis of studies worldwide, as is apparent, for example, in F. Sulu-Gambari et al., "Cable Bacterial Control Iron-Phosphorus Dynamics in Sediments of a Coastal Hypoxic Basin", Environmental Science & Technology, 2016, 50, 1227-1233 and M. Hermans et al., "Coupled dynamics of iron, manganese and phosphorus in brackish coastal sediments populated by cable bacteria", Limnology and Oceanography 9999, 2021, 1-21, with the latter paper also revealing that the effect is small. Presently, surprisingly, it has been found that combination with an alkaline earth metal peroxide, more particularly calcium peroxide, enables the formation of vivianite. Formation of apatite, as a P-rich precursor, serves here as a condensation nucleus and/or catalytically, in order to be able to react with Fe(II), which can be supplied and/or can be released from the reduction of Fe(III), for example during or after consumption of the alkaline earth metal peroxide, in a sediment which is then seasonally hypoxic, for example. Accordingly, the formation of vivianite can take place successively as a stabilizing mechanism, after the end of sediment oxidation, for example, and hence is able to fix not only the Fe(II) itself but also the phosphate bound beforehand, with Fe(III) for example.

There is no particular restriction on the introduction and/or application of the composition comprising the at least one alkaline earth metal peroxide, more particularly calcium peroxide. According to certain embodiments, the composition comprising at least one alkaline earth metal peroxide is introduced into and/or applied to the water, the sludge and/or the sediment directly, in solid form or as an aqueous suspension or solution, by hand or by suitable metering systems. This is easy to implement and enables a distribution, so that approximately equal concentrations of alkaline earth metal peroxide, more particularly calcium peroxide, are available within the waters, on the sludge and/or the sediment, even over long periods, and vivianite is enabled to form evenly. It has surprisingly been found that by the introduction and/or application of the composition comprising the at least one alkaline earth metal peroxide, more particularly calcium peroxide, vivianite formation is promoted and vivianite is formed in a form which can easily be removed from the waterbody, sediment and/or sludge.

There is no particular restriction on the composition comprising at least one alkaline earth metal peroxide, and according to certain preferred embodiments it comprises only one alkaline earth metal peroxide, more particularly calcium peroxide. According to certain embodiments it is possible for there to be more than one alkaline earth metal peroxide in the composition.

According to certain embodiments, the composition comprising at least one alkaline earth metal peroxide is present in solid form, and the waterbody to be treated flows around it. In this way the at least one alkaline earth metal peroxide, more particularly calcium peroxide, is able to release oxygen evenly over long periods, hence enabling longer intervals between introduction. According to certain embodiments, the composition comprising at least one alkaline earth metal peroxide is present in solid form and is mixed with the waterbody. This enables a homogeneous distribution in the waterbody, and hence an evenly distributed formation of vivianite.

According to certain embodiments the composition comprising at least one alkaline earth metal peroxide is introduced, or else incorporated according to certain embodiments, into the sediment and/or the sludge by positive mixers, rotary tillers or other mechanical metering systems and/or methods. In this way the sediment and/or the sludge can be loosened and its surface area increased for the formation of vivianite.

Step (a) may generally be accomplished by directly metering the components by hand, and/or by technical devices or accessories such as metering systems. The material may be metered directly into the waterbody or water, the sludge and/or the sediment to be treated, and/or else by means of containers which contain material in solid form and through which the water to be treated flows, such as, for example, filter cartridges or fixed-bed or fluidized-bed reactors.

Suitable alkaline earth metal peroxides are, for example, the peroxides of magnesium and calcium, and mixtures thereof, with preference being given to the use of peroxides of calcium and magnesium or mixtures thereof. Particularly preferred are calcium peroxides, where calcium may be replaced by magnesium in proportions of 0.02 wt % to 50 wt %, preferably up to 30 wt %, based on $CaO_2$. Especially preferred is calcium peroxide, which is able to release oxygen over long periods. In commercially customary products, the alkaline earth metal peroxide is typically present in a mixture with the corresponding carbonate and hydroxide.

According to certain embodiments the composition comprising at least one alkaline earth metal peroxide further comprises at least one alkaline earth metal carbonate and/or at least one alkaline earth metal hydroxide and/or an alkaline earth metal sulfate. Besides calcium peroxide, for example, calcium carbonate, calcium hydroxide and/or magnesium sulfate may be included. Illustrative compositions with such constituents are, for example, IXPER® 75C from Solvay. Illustrative suitable compositions comprising alkaline earth metal peroxide are, furthermore, SchlixX® and SchlixX® plus from Söll GmbH.

According to certain embodiments the at least one alkaline earth metal peroxide is used in a mixture with alkali metal carbonate peroxyhydrate. Alkali metal carbonate peroxyhydrates are known, when used in water at a rate of 5-20 g/m$^3$, to have a directly oxygen-increasing effect, with as yet no biocidal effect occurring. The alkali metal carbonate peroxyhydrates are adducts of alkali metal carbonates with $H_2O_2$, such as $Me_2CO_3 \times H_2O_2$, for example 2 $Me_2CO_3 \cdot 3H_2O_2$ (Me=alkali metal, for example Na, K, Rb, Cs, more particularly Na). They are also referred to as alkali metal percarbonates and are available commercially. From both an economic and an environmental standpoint, sodium carbonate peroxyhydrate has proven to be particularly suitable in order to achieve immediate increase of low oxygen contents in the body of water.

According to certain embodiments the composition comprising at least one alkaline earth metal peroxide further comprises at least one alkali metal carbonate peroxyhydrate, more particularly $Na_2CO_3 \times H_2O_2$, preferably $2Na_2CO_3 \cdot 3H_2O_2$, or a mixture of $Na_2CO_3$ and $H_2O_2$. According to certain embodiments the process of the invention further comprises introducing and/or applying at least one alkali metal carbonate peroxyhydrate, more particularly $Na_2CO_3 \times H_2O_2$, preferably $2Na_2CO_3 \cdot 3H_2O_2$, or a mixture of $Na_2CO_3$ and $H_2O_2$.

The alkaline earth metal peroxides and alkali metal carbonate peroxyhydrates are used preferably in proportions of 1:1 to 1:0.03.

A boost to phosphate precipitation may be achieved if lanthanum ions are added to the system to be treated. This combination is particularly useful if phosphate precipitation is also indicated anyway for the purpose of reducing the eutrophication.

Lanthanum in the active sediment barrier reduces the outflow of phosphorus from the sediment if the sediment becomes reducing again after the $CaO_2$ treatment.

For implementation of the process of the invention, the substances used, i.e. alkaline earth metal peroxides and optionally alkali metal carbonate peroxyhydrates and also further optional constituents, are applied according to certain embodiments in an amount of 2 to 700, preferably 4 to 500, more particularly 5 to 300, very preferably 10 to 150, g/m$^2$ of water area. In the case of the treatment of sediment and/or sludges it is possible, owing to the typically higher quantity of oxidizable substances, for the addition of the substances used in the invention to be a multiple of the amount to be added to waterbodies. In these cases a repeated use may be carried out, for the increased formation of vivianite.

The at least one alkaline earth metal peroxide used in the invention, and further components used optionally, may be added to the systems to be treated either in the form of individual substances or in a mixture with others in a solid, in aqueous solutions or slurries.

Solids of this kind which are contemplated include, in particular, silicates, such as phyllosilicates or tectosilicates, preferably from the group of the zeolites and bentonites. For performance reasons it is particularly useful to compact the materials present in solid form and to use them, for example, as granules, pellets or tablets. According to certain embodiments, therefore, the composition comprising at least one alkaline earth metal peroxide further comprises at least one silicate, such as phyllosilicates or tectosilicates, preferably from the group of the zeolites and bentonites.

Depending on the water quality and sediment quality, such as carbonate content, pH, etc., it may be appropriate to add still further compounds which increase the water or sediment quality. Examples of such compounds include $Ca(OH)_2$, $CaO$, $CaCO_3$, $CaCl_2$, $Ca(NO_3)_2$, $CaSO_4$, $MgSO_4$, $Ca_2SiO_4$, further, analogous magnesium compounds, and also mixtures of the aforementioned. Depending on the nature of the untreated water it may be necessary to treat the waterbody, the sediment and/or the sludge using alkali metal salts or alkaline earth metal salts, more particularly oxides, hydroxides, carbonates and/or hydrogencarbonates, in order, for example, to control the pH.

According to certain embodiments, the compounds used in the invention are used in combination with a mixture of $CaCO_3$, $CaCl_2$ and/or $Ca(NO_3)_2$ and optionally magnesium salts, and also $NaHCO_3$ and optionally $KHCO_3$, where $CaCO_3$ and $CaCl_2$ and/or $Ca(NO_3)_2$ and also optionally magnesium salts are present in a molar ratio of 0.01:1 to 2:1 and $CaCl_2$ and/or $Ca(NO_3)_2$ and also optionally magnesium salts and $NaHCO_3$ and also optionally $KHCO_3$ are present in a molar ratio of 1:3 to 2:1. A mixture of this kind and its suitability for the treatment of waters and sediments is described for example in European Patent Application EP 737 169. According to certain embodiments the composition comprising at least one alkaline earth metal peroxide is additionally used with a mixture of $CaCO_3$, $CaCl_2$ and/or $Ca(NO_3)_2$ and optionally magnesium salts, and also $NaHCO_3$ and optionally $KHCO_3$, where $CaCO_3$ and $CaCl_2$ and/or $Ca(NO_3)_2$ and also optionally magnesium salts are present in a molar ratio of 0.01:1 to 2:1 and $CaCl_2$ and/or $Ca(NO_3)_2$ and also optionally magnesium salts and $NaHCO_3$ and also optionally $KHCO_3$ are present in a molar ratio of 1:3 to 2:1.

There is no particular restriction on the formation of vivianite in the waterbody, sediment and/or sludge in step (b). Where iron ions, more particularly $Fe^{2+}$ ions, are present in the waterbody, sediment and/or sludge, the formation of vivianite may take place simply by passage of time, it being advantageous here if cable bacteria are present, which, moreover, are able to further promote the formation of vivianite through a sulfur cycle.

Where there are not sufficient iron ions present, and/or else in order to produce further forcing of formation of iron, it is also possible according to certain embodiments for iron ions, more particularly $Fe^{2+}$ ions, to be introduced and/or applied. According to certain embodiments, iron ions, more particularly $Fe^{2+}$ ions, are introduced and/or applied additionally in step (b) and/or before and/or after step (b), preferably in step (b) and/or after step (b). The introduction and/or application may take place in parallel with the introduction and/or application of a composition comprising at least one alkaline earth metal peroxide into and/or to the waterbody, the sediment and/or the sludge, or else consecutively, i.e. thereafter, for example within 24 h or less, 12 h or less, or even 6 h or less.

It is advantageous if there are cable bacteria present in step (b) in the waterbody, sediment and/or sludge. For this purpose it is also possible, optionally, for an investigation to take place prior to step (a) and/or (b) in order to find out whether cable bacteria are present, and also, preferably, whether they are present in sufficient concentration/density. Where cable bacteria are not present, or are not present in sufficient concentration, they can, according to certain embodiments, be introduced and/or the growth/multiplication of the cable bacteria can be stimulated by suitable measures. According to certain embodiments, for example, in the case of a low density of cable bacteria (e.g., $<10^1$ cells/$cm^2$ or $<100$ cells/$m^2$), a small dose of calcium peroxide may first be delivered, in order to develop an in situ preculture, before, for example at the earliest 2 months, 3 months or 4 months later, a second delivery takes place.

There is further no particular restriction on the optional introduction of cable bacteria. They may be introduced, for example, as a suspension with water as solvent. Since the cable bacteria are able to reproduce very well, particularly under sufficient substrate conditions ($O_2/S^{2-}$), the concentrations required for effective inoculation are not very high; with $10^2$ to $10^5$ cells/mL, for example, just a few litres of a corresponding preculture, e.g. 2, 3, 4, 5, 6, 7, 8, 9, or 10 litres or more, are sufficient for 1 ha of water area. Higher starting concentrations or quantities shorten the establishment time. Nor is there any particular restriction on the cable bacteria, which may be tailored, for example, to the type of waterbody. They may be provided, for example, from a preculture which can be cultured in the laboratory or in the field, on a partial area or total area of the waterbody. According to certain embodiments step (b) comprises introducing cable bacteria into the waterbody, the sediment and/or the sludge.

There is likewise no particular restriction on the investigation of the waterbody, sediment and/or sludge for the presence of cable bacteria, but such study is carried out before the respective steps of introducing and/or applying in step (a) and/or before the optional introduction of cable bacteria, since the introduction is dependent on the investigation results, and so normally the investigation results are awaited. The investigation may be made, for example, by the taking of a sample comprising solids, e.g. suspended substances, sludges, sediments, and subjecting the sample to microbiological investigation for cable bacteria, such as, for example, by investigation using cable bacteria-specific markers, e.g. with optical methods such as FISH (fluorescence in situ hybridization), by gene sequencing of genomes or genes present in the sample, etc. There is no particular restriction on the microbiological investigation, which may for example also comprise diverse preparatory steps such as purification and/or concentration steps, for instance.

If sufficient cable bacteria are found in a sample, it is no longer necessary to introduce cable bacteria. Where, however, no cable bacteria, or substantially no cable bacteria, e.g. $<10^1$ cells/$cm^2$ or $<100$ cells/$m^2$, are found, these bacteria are to be introduced and/or their growth is to be stimulated, as set out.

The introduction and/or application of a composition comprising at least one alkaline earth metal peroxide into and/or to the waterbody, the sediment and/or the sludge, and the optional introduction of cable bacteria, may be carried out independently of one another or simultaneously. Where cable bacteria are introduced, they are preferably, however, introduced such that the cable bacteria are able immediately to commence the utilization of the oxygen released by the at least one alkaline earth metal peroxide, more particularly calcium peroxide, and/or utilization of other electron acceptors provided by said peroxide, an example of an electron acceptor being the alkaline earth metal peroxide, e.g. calcium peroxide, itself. There is no particular restriction in this case on the time spacing between the introduction of the cable bacteria and step (a), although it may, for example, be up to a week, preferably up to 3 days, 2 days, 1 day or less, for example 12 h and less or 8 h and less.

Cable bacteria prefer a more pH-neutral environment. Since the pH in an uppermost layer may increase temporarily immediately after the delivery of an alkaline earth metal peroxide, more particularly calcium peroxide, the pH at a sediment phase boundary is preferably observed until it has normalized to values of between 8.7 and 7.4, for example before cable bacteria are introduced.

Calcium peroxide in particular can be processed as a product in, for example the above, compositions in such a way that there is no likelihood of increased pH on introduction, this being advantageous for the practical implementation of the invention.

The compositions comprising at least one alkaline earth metal peroxide and the cable bacteria, where they are introduced, are introduced preferably at substantially identical places or at the same place into the waterbody, the sediment and/or the sludge, in order to minimize diffusion events and to increase the efficiency of vivianite formation. In evidence in this case in particular is the synergy between the release of oxygen by the at least one alkaline earth metal peroxide, more particularly calcium peroxide, and/or by other electron acceptors derived from alkaline earth metal peroxide, e.g. calcium peroxide, and the use thereof by the cable bacteria, which then further promote the formation of vivianite.

According to certain embodiments, cable bacteria are introduced in such a way that they are able to accumulate on a sludge in a waterbody, deposits, sludges in general, sediments, etc., and so enable contacting of suboxic and/or anoxic regions of the material and of the oxygen released by the at least one alkaline earth metal peroxide, more particularly calcium peroxide, and/or by a different solid electron acceptor derived therefrom, for example the alkaline earth metal peroxide, e.g. $CaO_2$, itself, since in that case the formation of vivianite is promoted there via redox events.

In the process of the invention there is additionally no particular restriction on the optional magnetic removal of the vivianite from the waterbody, sediment and/or sludge in the optional step (c). For example, a suitable magnetic separating apparatus comprising a magnet may be introduced into the waterbody, the sediment and/or the sludge; the magnetic separating apparatus comprising a magnet may be brought into the vicinity of the waterbody, sediment and/or sludge in such a way that vivianite can be removed from the waterbody, sediment and/or sludge by a magnetic field which is provided and/or generated; or the waterbody, the sediment and/or the sludge may be applied to the magnetic separating apparatus comprising a magnet, and/or may be introduced into the magnetic separating apparatus comprising a magnet.

The latter steps in particular may be integrated in the case, for example, of wastewater purification in a sewage treatment plant.

There is likewise no particular restriction on the magnetic separating apparatus comprising the magnet. The magnet may for example be a permamagnet or an electromagnet. A plurality of magnets may also be provided. The separating apparatus may additionally comprise mounts, a housing, conveying means such as a conveyor belt or a winch, etc., and may be adapted according to whether the underlying system in the context of vivianite removal is a waterbody, a sediment or a sludge.

The process of the invention may be used for all conceivable waterbodies, sludges and/or sediments. It may be used, for example, for obtaining vivianite in waterbody sediments, sludges and/or water/wastewater in open and closed aqueous systems, waterbodies such as seawater, brackish water and freshwater, for example in reservoirs, artificial or natural lakes, waterbodies for bathing or fishery, ornamental ponds and aquaria, and also in process waters, examples being sewage treatment plants, wastewater treatment plants, recycling plants, cooling water plants and heat exchanger plants, wastewaters of chemical production plants, or in water which results from processes of decomposition and condensation (e.g. landfill leachate water or condensate from thermal waste utilization plants) or by leaching processes (e.g. water which percolates through contaminated soils, waterbody sediments or sludges).

Figures 1, 2:
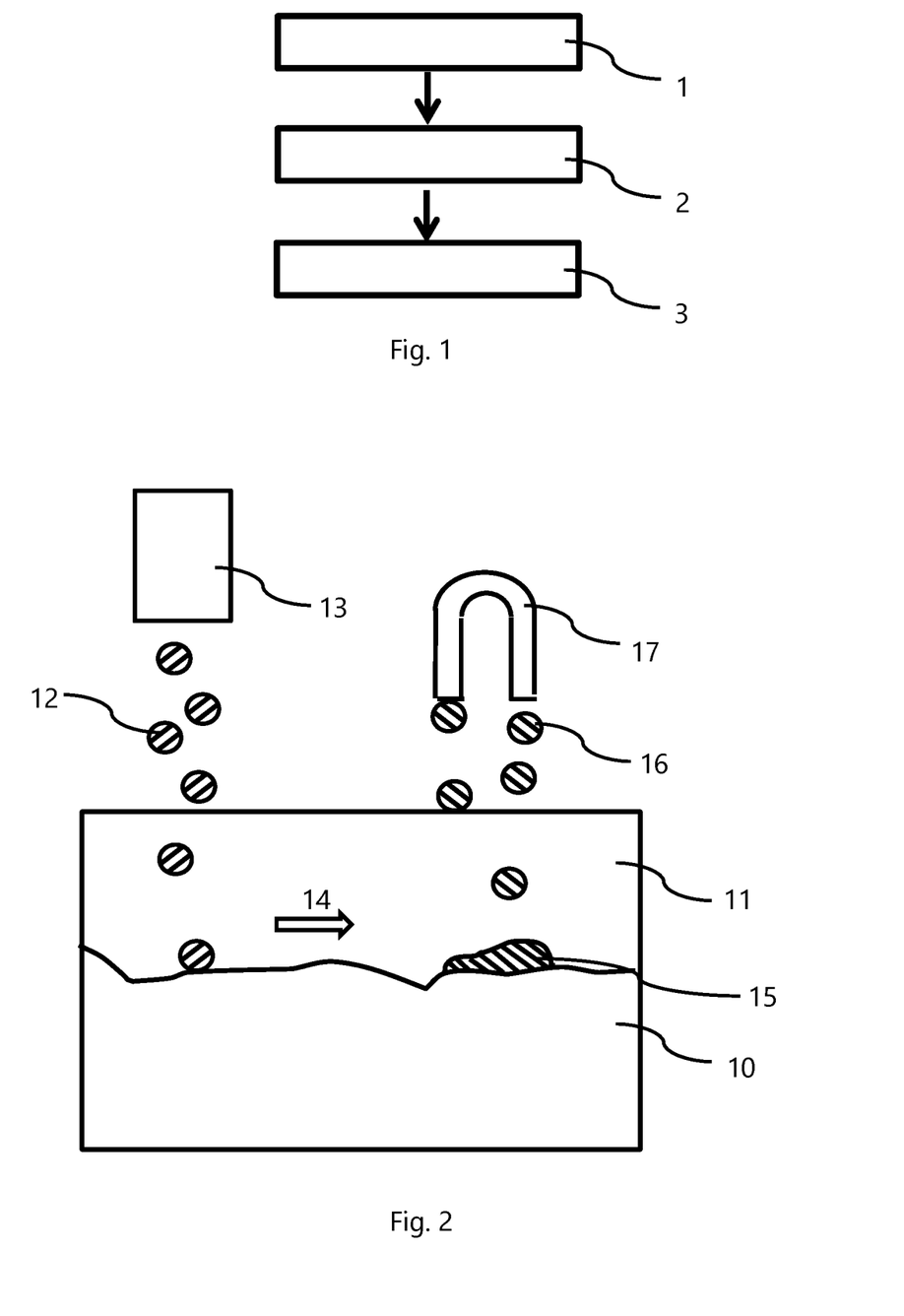
FIG. 1 shows schematically an illustrative process of the invention according to the first aspect.
FIG. 2 shows schematically an illustrative apparatus of the invention according to the second aspect.

An illustrative process of the invention is shown schematically in FIG. 1. The introduction and/or application of a composition comprising at least one alkaline earth metal peroxide 1 into and/or to a waterbody, a sediment and/or a sludge (step (a)) is followed by formation of vivianite 2 in the waterbody, sediment and/or sludge (step (b)), and also by magnetic removal of the vivianite 3 from the waterbody, sediment and/or sludge (step (c)).

In a further aspect the present invention relates to an apparatus for obtaining vivianite from a phosphorus-containing waterbody, sediment and/or sludge, comprising:
  (i) a device for introducing and/or applying a composition comprising at least one alkaline earth metal peroxide, configured to introduce the composition comprising at least one alkaline earth metal peroxide into the waterbody, the sediment and/or the sludge and/or to apply it to the waterbody, the sediment and/or the sludge; and
  (ii) a magnetic separating apparatus comprising a magnet, configured to remove the vivianite from the waterbody, sediment and/or sludge.

The apparatus of the invention can be used in particular to carry out the process of the invention. Accordingly, certain embodiments, configurations and developments of the process are also applicable in the context of the apparatus of the invention, and vice versa.

In the apparatus of the invention there is no particular restriction on the device for introducing and/or applying a composition comprising at least one alkaline earth metal peroxide, configured to introduce the composition comprising at least one alkaline earth metal peroxide into the waterbody, the sediment and/or the sludge and/or to apply it to the waterbody, the sediment and/or the sludge. According to certain embodiments the device for introducing and/or applying a composition comprising at least one alkaline earth metal peroxide comprises the composition comprising at least one alkaline earth metal peroxide. The composition comprising at least one alkaline earth metal peroxide may in this case, according to certain embodiments, have a nature such in particular as described in connection with the process of the invention.

According to certain embodiments the device for introducing and/or applying a composition comprising at least one alkaline earth metal peroxide comprises a metering device, configured for metering the composition comprising at least one alkaline earth metal peroxide. There is no particular restriction on the metering device. According to certain embodiments, the metering device is designed in such a way that it enables the composition comprising at least one alkaline earth metal peroxide to be introduced substantially consistently or consistently in terms of time. For this purpose the metering device may be shaped appropriately, by use of complex structures, for instance, and/or may comprise corresponding release elements such as controlled valves, etc., for instance.

Besides this, there is likewise no particular restriction on the magnetic separating apparatus comprising a magnet and configured for removing the vivianite from the waterbody, sediment and/or sludge. The magnet may for example be a permamagnet or an electromagnet. There may also be multiple magnets provided. The separating apparatus, furthermore, may comprise mounts, a housing, conveying means such as a conveyor belt or a winch, etc., and may be adapted according to whether the underlying system in the case of vivianite removal is a waterbody, a sediment or a sludge.

According to certain embodiments the apparatus of the invention further comprises a positive mixer and/or a rotary tiller designed for introducing, more particularly incorporating, the composition comprising at least one alkaline earth metal peroxide into a sediment and/or sludge. There are no particular restrictions on the positive mixer and the rotary tiller.

An illustrative apparatus of the invention is shown schematically in FIG. 2.

Situated on an anoxic sediment 10 comprising cable bacteria there is a phosphate-containing waterbody 11. A composition comprising at least one alkaline earth metal peroxide 12 is metered via a device for introducing and/or applying a composition comprising at least one alkaline earth metal peroxide 13. Vivianite 15 is formed in the waterbody 11, and is removed from the waterbody in the form of particles 16 by means of a magnetic separating apparatus comprising a magnet 17.

A further aspect of the present invention is directed to the use of a composition comprising at least one alkaline earth metal peroxide and of a magnetic separating apparatus for obtaining vivianite from a phosphorus-containing waterbody, sediment and/or sludge. The composition comprising at least one alkaline earth metal peroxide is of a nature here, in particular, such as described in connection with the process of the invention and the apparatus of the invention. The magnetic separating apparatus as well is more particularly of a nature as described in connection with the process of the invention and the apparatus of the invention.

The embodiments and developments above may be combined arbitrarily with one another in so far as is rational. Further possible embodiments, developments and implementations of the invention also encompass combinations, not explicitly stated, of features of the invention described above or below in relation to the working examples. In this case in particular the skilled person will also add individual aspects as improvements or additions to the respective basic form of the present invention.

The invention is described further in detail subsequently with reference to various examples thereof. The invention, however, is not limited to these examples.

For the following examples the following measurements were conducted:

XRD: according to DIN EN 13925-1, -2:2003 and -3:2005, and also DIN EN 1330-11:2008. For measurements, the surface was straightened after filling and aligned against a blade in the ray. Measurement was made with Bragg-Brentano geometry with an STOE 0/9 diffractometer in reflection mode, using radiation of a Co K$\alpha$1.2 source with $\lambda\sim$1.79021 Å, U=40 kV, I=1.35 mA.

FT-IR spectroscopy was carried out with a Nicolet iN10/Nicolet iZ10 spectrometer from Thermo Scientific in ATR mode with KBr pellets and with a Jasco FT/IR-4100 spectrometer having an SR-ATR unit with a single diamond crystal, under constant pressure with DLATGS detector.

Orthophosphate was measured according to DIN EN ISO 6878. Dissolved oxygen and the pH were determined using an HQ40 digital multimeter (Hach Lange GmbH), and micrographs were recorded with a Zeiss Axioskop 40 with a Canon EOS 600D with an EFS 18-55 mm lens.

Reference Example 1: Phosphate Binding Capacity of Calcium Peroxide

To obtain the phosphate binding capacity of $CaO_2$, 7.16 g (53 mmol) of potassium dihydrogenphosphate were added to a 10 L batch of deionized water. A subsequent orthophosphate measurement according to DIN EN ISO 6878 gave a dissolved phosphate content of 0.5 g/l (5.3 mmol/L). This phosphate-containing solution was admixed with 5.0 g of a calcium peroxide (52 mmol of pure $CaO_2$). Immediately after the addition, the solution turned hazy, and the evolution of gas was visible. After 24 hours of stirring at medium speed (500 rpm), the suspension was filtered through a round filter (MN 614, 240 mm diameter). The filter residue was dried at 60° C. over 24 hours and the filtrate was subjected to further phosphate measurement. The orthophosphate content of the filtrate after exposure to calcium peroxide for 24 hours was determined as 0.004 mg/L, corresponding to a stoichiometric binding capacity of around 0.1 g of phosphate per 1 g of calcium peroxide.

The dried residue (8.1 g, consisting of calcium peroxide+phosphate; hereinafter HA 1) was stored for the following examples and analysed by means of XRD and FT-IR spectroscopy.

The calcium peroxide starting material (tradename Ixper®) was likewise analysed and was identified as such.

Reference Example 2: Phosphate Dissolution Experiments

In order to simulate possible redissolution in a natural environment, sediment cores and their supernatant water were taken from the Mühlteich (millpond) in the vicinity of Haldensleben and placed into tubes. The test was conducted with blank samples (without addition of HA 1 or dithionite), samples with HA 1 (without addition of dithionite) (as sodium dithionite for establishing a reducing environment) and samples with HA 1+dithionite. All samples were carried out in duplicate. Because of the different amount of sediment in the tubes, all of the tubes were measured in order to determine the precise dosage. Over 3 weeks the amount of orthophosphate (hereinafter also $PO_4$), the pH and dissolved oxygen (DO), in the supernatant were monitored. The results are shown in Table 1.

TABLE 1

Measurement results in Reference Example 2

| | Blank sample | | | HA 1 | | | HA 1 + dithionite | | |
|---|---|---|---|---|---|---|---|---|---|
| Time [h] | $PO_4$ [mg/L] | pH | DO [mg/L] | $PO_4$ [mg/L] | pH | DO [mg/L] | $PO_4$ [mg/L] | pH | DO [mg/L] |
| 0 | 1.40 | 6.99 | 0.53 | 1.06 | 7.15 | 0.37 | 0.51 | 7.45 | 0.11 |
| 1 | 1.54 | 7.01 | 0.91 | 1.21 | 10.20 | 16.28 | 9.2 | 7.38 | 0.19 |

TABLE 1-continued

Measurement results in Reference Example 2

| | Blank sample | | | HA 1 | | | HA 1 + dithionite | | |
|---|---|---|---|---|---|---|---|---|---|
| Time [h] | PO$_4$ [mg/L] | pH | DO [mg/L] | PO$_4$ [mg/L] | pH | DO [mg/L] | PO$_4$ [mg/L] | pH | DO [mg/L] |
| 24 | 1.96 | 7.16 | 0.62 | 0.98 | 11.07 | 16.18 | 10.15 | 7.27 | 0.19 |
| 72 | 2.30 | 7.10 | 0.53 | 0.61 | 11.13 | 13.66 | 28.15 | 5.26 | 0.20 |
| 168 | 1.47 | 7.13 | 0.55 | 0.18 | 11.47 | 8.06 | 60.35 | 5.64 | 0.18 |
| 336 | 1.53 | 6.99 | 0.62 | 0.19 | 11.46 | 5.38 | 121 | 5.71 | 0.41 |
| 504 | 1.32 | 7.84 | 1.18 | 0.20 | 11.25 | 5.33 | 122 | 5.56 | 0.80 |

It was found that under natural conditions no phosphates are redissolved in the sediment. In addition, in the test columns with dithionite, blueish vivianite crystals were formed. All further examples are based on these experiments.

Example 1: Vivianite Formation and Removal

As in the reference example HA 1 was placed into a reducing environment. A model sediment core of sand with a supernatant consisting of deionized water was used, and dithionite and iron in the form of iron(II) sulfate were added. The concentrations in the supernatant per 1 litre of deionized water was as follows:
4.97 g (18 mmol) of iron(II) sulfate*6H$_2$O
1 g of sodium dithionite An amount of 5 g (10 mmol) of dried HA 1 was added to this column and the column was sealed tightly for an experimental duration of 7 weeks.

After a number of weeks, blueish crystals were formed on the upper sediment layer. After the total experimental duration of 7 weeks, the supernatant was separated from the sediment core by decanting under an argon atmosphere. The sediment was filtered and dried. The dried blue crystals were then separated from the sand using an yttrium magnet and a paper between magnet and sediment. The blue particles (quantity 100 mg) were additionally investigated using XRD measurements and FT-IR spectroscopy, and confirmed as vivianite.

It was found that there was a conversion of hydroxylapatite to vivianite in accordance with the following formula:

$2Ca_5(PO_4)_3(OH)+9FeSO_4*7H_2O \rightleftarrows CaOH+ 9CaSO_4*2H_2O+3Fe_3(PO_4)_2*8H_2O$ Further experiments were conducted in order to find the correct parameters for the formation of vivianite, and in the subsequent examples vivianite was also removed by magnet as in Example 1.

Example 2

HA 1 (2 g, 4 mmol) was added to 300 mL of ultrapure water in an Erlenmeyer flask. The resulting suspension was flushed with argon until the oxygen content was below the detection limit of 0.02 mg/L (around 15 min). Under an argon atmosphere 0.3 g (1.7 mmol) of sodium dithionite and 5 g (18 mmol) of iron(II) sulfate heptahydrate were added. The flask was sealed and the suspension was stirred at room temperature at a medium rotary speed (around 300 rpm). Over the course of 3 weeks, the precipitate turned grey in colour and after 3 weeks was filtered, rinsed thoroughly with water and dried at 60° C. over 24 h. During this procedure, the grey precipitate transformed into a deep turquoise. 1.6 g were obtained and were analysed by XRD and IR spectroscopy, again confirming the formation of vivianite and the formation of the hydroxylapatite precursor and also gypsum (gypsum:vivianite:hydroxylapatite ratio w/w=60:10:30).

Example 3

HA 1 (2 g, 4 mmol) was admixed with 300 mL of ultrapure water in an Erlenmeyer flask. The resulting suspension was flushed with argon until the oxygen content was below the detection limit of 0.02 mg/L (around 15 min). Under an argon atmosphere 5 g (18 mmol) of iron(II) sulfate heptahydrate were added. The flask was sealed and the suspension was stirred at room temperature at a medium rotary speed (around 300 rpm). Over the course of 3 weeks, the precipitate turned grey in colour and after 3 weeks was filtered, rinsed thoroughly with water and dried at 60° C. over 24 h. 1.4 g were obtained and were analysed by XRD and IR spectroscopy, again confirming the formation of vivianite and the formation of the hydroxylapatite precursor and also gypsum (gypsum:vivianite:hydroxylapatite ratio w/w=12.7:30.8:56.5).

Example 4

HA 1 (4 g, 8 mmol) was admixed with 600 mL of ultrapure water in an Erlenmeyer flask. Then 0.6 g (3.4 mmol) of sodium dithionite and 10 g (36 mmol) of iron(II) sulfate heptahydrate were added. The flask was sealed and the suspension was shaken at a low rotary speed (around 90 rpm) at room temperature. Over the course of 3 weeks, the precipitate turned a turquoise colour, and after 3 weeks it was filtered, rinsed thoroughly with water and dried at 60° C. over 24 h. During this procedure, the otherwise grey precipitate transformed into a deep turquoise. 2.3 g were obtained and were analysed by IR spectroscopy. The mixture obtained shows the absorption bands typical for vivianite at 3400-3300 cm$^{-1}$, ~1625 cm$^{-1}$, ~1040 cm$^{-1}$ and 970 cm$^{-1}$.

Example 5

600 mL of ultrapure water were added to HA 1 (4 g, 8 mmol) in an Erlenmyeyer flask. The resulting suspension was flushed with argon until the oxygen content was below the detection limit of 0.02 mg/l (around 15 min). Under argon atmosphere, 10 g (36 mmol) of iron(II) sulfate heptahydrate were added. The flask was sealed and the suspension was shaken at a low rotary speed (around 90 rpm) at room temperature. Over the course of 3 weeks, the precipitate turned grey, and after 3 weeks it was filtered, rinsed thoroughly with water and dried at 60° C. over 24 h. 2.1 g were obtained and were analysed by IR spectroscopy. The mixture obtained shows the typical absorption bands of vivianite at 3400-3300 cm$^{-1}$, ~1625 cm$^{-1}$ and ~1040 cm$^{-1}$.

When the parameters defined were monitored, it became clear that under natural conditions phosphate is bound in the newly formed mineral HA 1. The synthesised HA 1 additionally appears to bind even more phosphate. While the concentrations of the blank samples fluctuate between 1.5 and 2 mg/L, the concentration of orthophosphate in the samples treated with HA 1 drops to 0.2 mg/L, which can be interpreted by an incomplete first reaction and traces of $CaO_2$. There is also an increase in the oxygen content and the pH of the samples treated with HA 1, which is attributable to the presence of residual peroxide and the reaction of the peroxide with water to form $Ca(OH)_2$ with release of $O_2$. These traces of $CaO_2$ are also responsible for the accelerated formation of hydrogensulfite ($HSO_3^-$) and hydrogensulfate ($HSO_4^-$) from sodium dithionite in accordance with the following chemical equation:

$$Na_2S_2O_4 + H_2O + O_2 \rightleftharpoons NaHSO_3 + NaHSO_4$$

What is claimed is:

1. A process for forming and obtaining vivianite in and/or from a phosphorus-containing waterbody, sediment and/or sludge comprising anoxic zones, the process comprising the steps of:
   (a) introducing and/or applying a composition comprising $Fe^{2+}$ ions and at least one alkaline earth metal peroxide into and/or to the waterbody, the sediment and/or the sludge;
   (b) introducing cable bacteria into the waterbody, the sediment and/or the sludge and forming vivianite in the waterbody, sediment and/or sludge; and
   (c) magnetically removing the vivianite formed from the waterbody, sediment and/or sludge;
   wherein the alkaline earth metal peroxide is calcium peroxide.

2. The process according to claim 1, wherein the composition further comprises at least one selected from the group consisting of an alkaline earth metal carbonate, an alkaline earth metal hydroxide, and an alkaline earth metal sulfate.

3. The process according to claim 1, wherein the composition further comprises at least one alkali metal carbonate peroxyhydrate or a mixture of $Na_2CO_3$ and $H_2O_2$, or further comprises introducing and/or applying at least one alkali metal carbonate peroxyhydrate or a mixture of $Na_2CO_3$ and $H_2O_2$ in step (a).

4. The process according to claim 3, wherein the at least one alkali metal carbonate peroxyhydrate is $Na_2CO_3 \times H_2O_2$.

5. The process according to claim 4, wherein the $Na_2CO_3 \times H_2O_2$ is $2Na_2CO_3 \cdot 3H_2O_2$.

6. The process according to claim 3, wherein the calcium peroxide and the at least one alkali metal carbonate peroxyhydrate are applied in an amount of 2 to 700 g/m² area of the waterbody.

7. The process according to claim 1, wherein the composition further comprises a mixture of $CaCO_3$, $CaCl_2$) and/or $Ca(NO_3)_2$ and optionally magnesium salts, $NaHCO_3$ or $KHCO_3$.

8. The process according to claim 1, wherein the composition further comprises at least one silicate.

9. The process according to claim 8, wherein the at least one silicate is selected from phyllosilicates or tectosilicates.

10. The process according to claim 9, wherein the phyllosilicates or tectosilicates are selected from the group consisting of zeolites and bentonites.

11. The process according to claim 1, wherein the composition is applied to, and/or introduced into the waterbody, the sludge and/or the sediment directly, in solid form or as an aqueous slurry or solution, by hand or by suitable metering systems.

12. The process according to claim 1, wherein the composition is present in solid form and is mixed with the waterbody or the waterbody flows around it.

13. The process according to claim 1, wherein the composition is introduced by positive mixers, rotary tillers or other mechanical metering devices and/or methods into the sediment and/or the sludge.

14. The process according to claim 1, wherein magnetically removing the vivianite from the waterbody, sediment and/or sludge in step (c) comprises using a magnetic separating apparatus for obtaining the vivianite.

15. The process according to claim 1, further comprising observing a pH at a sediment phase boundary until it has normalized to pH values between 8.7 and 7.4 before introducing the cable bacteria.

* * * * *